United States Patent [19]

Mindick et al.

[11] 4,085,006
[45] Apr. 18, 1978

[54] AUTOMATIC CELL ANALYZER METHOD

[75] Inventors: Leo R. Mindick, Flushing, N.Y.; Avraham Bruck; Dan Inbar, both of Haifa, Israel; Leopold G. Koss, New York, N.Y.

[73] Assignee: Isomedics, Incorporated, Great Neck, N.Y.

[21] Appl. No.: 521,518

[22] Filed: Nov. 6, 1974
(Under 37 CFR 1.47)

[51] Int. Cl.² .......................... C12K 1/00; C12K 9/00
[52] U.S. Cl. .................................. 195/103.7; 195/127
[58] Field of Search .............................. 195/103.7, 127

[56] References Cited
U.S. PATENT DOCUMENTS 3,673,410  6/1972  Waite et al. ........................ 195/103.7
3,678,148  7/1972  Calola ................................. 195/103.7

Primary Examiner—Alvin E. Tanenholtz
Attorney, Agent, or Firm—Gottlieb, Rackman & Reisman

[57] ABSTRACT

A cell analyzer which automatically processes and evaluates cell samples for possible indications of malignancy and other abnormalities is disclosed. Cell samples are prepared in a suspension and are tagged with an appropriate radioactive stain or appropriate biochemical. Counting, filtering and drying steps under computer control are followed by the taking of a radioactive count with respect to a normalized number of cells. The results of the radioactive counting determine whether the particular sample is classified as "positive" or "negative".

3 Claims, 3 Drawing Figures

AUTOMATIC CELL ANALYZER METHOD

This invention relates to medical electronic equipment in general, and to an automatic system and device for analyzing and evaluating the number and character of certain cell samples.

In recent times, the problem of health and well being of the world's population has been receiving increasing attention. Of late, the scientific community has focused its energies on the application of sophisticated engineering principles to such problems. One of the principal goals of this general approach has been to alert the public to the benefits of preventive medicine, or at least to provide for early detection of serious diseases or body dysfunctions. Among the illnesses which have been uppermost in the minds of the scientific and medical professions have been respiratory diseases, heart ailments and various forms of cancer.

The concept of early detection has perhaps been most pronounced where cancer has been involved because of the well-established "danger signals" which can be noticed as possible symptoms or precursors of the disease. Thus, considerable attention has been given to various signs such as body lumps (e.g., in the breast), sores which do not heal, unusual bodily discharges and the like. While these symptoms are of the pragmatic type, lending themselves to detection by individuals without medical assistance, at least in the first instance, the scientific community has also made significant contributions to cancer detection and testing programs.

Probably the leading cancer detection and screening test known to medicine today is the "Pap" test, named in honor of Dr. George Papanicolaou, its principal developer. This test permits exfoliated cells to be withdrawn from various body regions, suitably washed and stained and then visually tested for specific parameters associated with carcinoma. Specifically, the Pap test can be utilized for cells taken from any mucosal surface of the body, but it is most widely known for use in connection with cervical cancer in women; it can also be applied with respect to cells taken from lung and rectal surfaces.

The basic principle on which the Pap test is based is that the nuclei of malignant or incipiently malignant cells are enlarged relative to the nuclei of "normal" cells—this is believed to be due to the greater amount of DNA and RNA in the nuclei. Accordingly, the Pap test teaches the use of nucleic stains which are attracted to and absorbed in the nuclei and cytoplasmic stains attracted to and absorbed in the cytoplasm. In the event that the nuclei are enlarged due to malignancy, greater quantities of the nucleic stain will be present in those nuclei. Since the nucleic stain used in the Pap test provides a visual contrast with the remainder of the cell (e.g., the cytoplasm, to which the nucleic stain does not generally attach), careful microscopic analysis of the cell samples after staining permits the cytologist or cytotechnician to evaluate the enlarged nuclei in the sample and ultimately make a determination that the sample is "negative" (no possible malignancy), "positive" (probable malignancy) or "suspicious" (questionable result requiring additional study).

However, despite the great advances achieved through the Pap test, leading to the early detection and often arresting of malignancies, a number of areas have been recognized as calling for improvement. In particular, the process is relatively time consuming, with a "good" screening (i.e., a microscopic evaluation, the recording of data, etc.) requiring 15 to 20 minutes. This is directly related to the realistic fatigue limitation of the cytologist or cytotechnician, permitting them to do only a few screenings in succession and requiring frequent rest periods to avoid errors or misreadings. Because of the time involved for each screening and the related fatigue problem, it is generally accepted that even a highly skilled technician can only review 50 cell samples in a given day. In addition, there is the very critical problem of accuracy—while the examination of individual samples under a microscope is fairly reliable, problems such as fatigue, stain failure (i.e., poor contrast), clumped cells and the like have caused scientists and doctors to look to other possible detection methods which would overcome these problems without sacrificing the accuracy offered by the Pap test.

The prior art has attempted to implement this general concern with a detection system such as that shown in U.S. Pat. No. 3,497,690, but that arrangement only detects fluorescence, which is energy from the visible spectrum, and therefore does not really avoid the optical problems alluded to above, most particularly "clumped cells". Flow-through devices are also known, using laser light for example; but this is also visible light and such systems have not tended to overcome the problems attendant upon the type of visualization used.

The broad concept of using the parameter of radioactive uptake of cells has also been considered in the past, with U.S. Pat. Nos. 3,673,410, 3,678,148 and 3,801,783 being the leading examples thereof. Those patents disclose the general approach of taking an "in vitro" specimen of cells from a patient, preliminarily treating the cells for analysis, applying a radioative stain which selectively attaches to the cell nuclei, making a normalized radiation count and evaluating the measured level of radioactivity as "positive", "negative" or "suspicious" for that specimen. Although the systems shown in the aforementioned patents disclose workable arrangements for implementation of the underlying concept, they do not provide the optimum design or workability for this highly advantageous principle. In particular, such prior art systems do not provide an efficient and integrated electromechanical arrangement for carefully performing and monitoring cell counting, cell washing, deposition and filtering, as well as radiation detection and readout. They also do not teach the more advantageous technique of cell separation and preparation for presentation to the system.

It is therefore an object of this invention to obviate one or more of the aforesaid difficulties.

It is also an object of this invention to utilize the size and radioactive level of a stained cell as a parameter to detect possible malignancy, or other abnormality.

It is another object of this invention to furnish a cell analyzer for rapidly and accurately performing radioactive detection on pre-measured quantities of cells in a sample.

It is a further object of this invention to provide an integrated electromechanical system for performing a variety of preparation, analysis and evaluation functions on cell samples.

The foregoing objects and advantages of this invention are obtained in an illustrative embodiment which comprises three principal components: an electromechanical sample handling apparatus, an instrument rack which includes the basic system electronics, counting mechanisms and computer control, and a data printer which provides both input instructions and readout. The cells which are presented to the system are initially processed, generally by an examining physician taking a conventional specimen, for example, of cervical cells. One group of such cells may be deposited upon a standard Pap smear slide, to be retained for subsequent microscopic analysis in the event the invention specifies that the cell sample is not "negative". The remaining cells obtained by the physician, nurse or technician are deposited in a fixation solution in a sample tube. Fixation is performed to inhibit the "clumping" of cells and it has been found that a preferred fixative is a solution of glutaraldehyde. The sample then is centrifuged, and the supernatant removed, leaving a "cell button". The "cell button" is then resuspended and the sample is subjected to ultrasonic treatment at a low frequency for a short time so as to further separate the cells but not to disrupt cell membrane integrity. This results in a satisfactory suspension of single cells which will further resist clumping and which will promote accurate counting by the invention. The radioactive stain is then added to the sample tube, with a preferable stain being acridine orange which has been rendered radioactive by the use of $c14$ atoms or other isotopes. The stained sample is then washed twice, centrifuged and after the supernatant portion of the liquid is decanted to remove unbound radioactive stain, the sample is ready for analysis.

The sample tubes are then placed in apertures in an upper plate of a sampler tray. The lower plate of the tray includes a plurality of sample filter assemblies corresponding in number and position to the sample tubes in the upper plate. The sampler tray is rotatable by an underlying motor having and can be indexed with respect thereto by appropriate mounting detents. The sample changer assembly further includes a sampler having an orifice tube designed to be periodically lowered into the sample tubes so that a pre-determined quantity of cells can be withdrawn therefrom, counted and then deposited on the corresponding sample filter on the lower plate of the sample changer tray. This sampling takes place after the sample changer assembly has been indexed to its first position under the control of the central processing unit. At this point, the orifice tube rotates into position over the first sample tube and is lowered into the tube, whereupon withdrawal of a pre-determined number of cells commences. This withdrawal is achieved by the suction applied from a pump located within the sample changer housing. During the suction, the cells are gradually deposited on the paper filter held in the sample filter assembly in the first position of the lower plate of the sample tray. In order to remove as much of the washing liquid as possible following deposition of the filter paper, a vacuum pump mates with the underside of the filter assembly and begins to draw vacuum after the pre-determined number of cells have been withdrawn from the sample tube and deposited on the filter. The sample tray then rotates to a second position and after being rinsed and ultrasonicated to avoid cross-contamination of samples, the sampler and orifice tube begin the withdrawal and counting process for the next sample. At the same time, the filter assembly containing the cells of the first sample is subjected to a heating and drying cycle at the second position to reduce radiation self-absorption and to enhance the radiation counting for the cells in the first sample. Thereafter, the sample changer advances to a third position with respect to the first sample, where a radioactive detector measures the radioactive level of that sample. The detected radiation level is transmitted to the processing unit which calculates the radioactive level normalized for the number of cells in the sample. A final reading is then provided to the data printer which furnishes a visual readout of all the relevant parameters of the cycle and gives a qualitative result for further evaluation by the cytologist or cytotechnician.

It is therefore a feature of an embodiment of this invention that an electromechanical sample mechanism is electronically and mechanically interfaced with a computer and data printer to provide sequential preparation, testing and evaluation of cell samples.

It is another object of an embodiment of this invention that cells withdrawn from a body orifice, cavity or the like are prepared for testing by placing them in a suspension, having them separated and then associated with a radioactive nucleic stain and placed into a sample tube for machine processing.

It is yet another object of an embodiment of this invention that a central computer processing unit controls the operation of a sample changer, a sampler tube, a cell counter, a radioactive detector and a readout mechanism, in an integral fashion to provide complete cell analysis.

It is a further feature of an embodiment of this invention that sample tubes containing prepared cells are placed on a sampler tray and a sampler tube is used to withdraw and count a pre-determined number of cells to be deposited on a corresponding filter for draining purposes, with the changer transporting the samplers sequentially from the counting and deposition position in a drying station and a radiation detector position.

These and other objects, features and advantages of this invention will become more readily understood when considered in connection with a presently preferred, but nonetheless illustrative, embodiment of the invention as explained in the following detailed description and as shown in the accompanying drawing, wherein.

Figure 1:
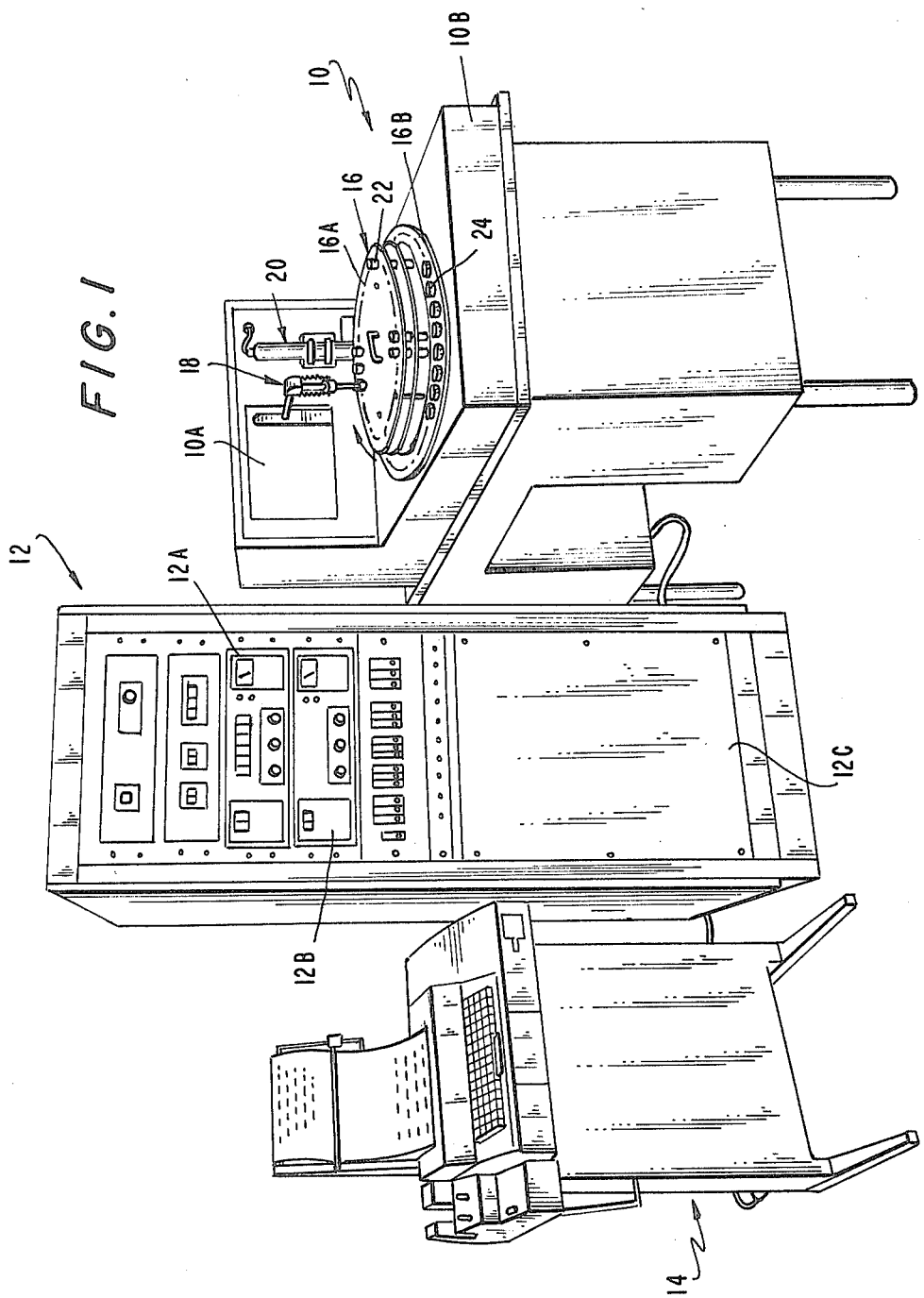
FIG. 1 is a general perspective view of the major components of the invention, including a data printer, the instrumentation rack including the computer and electronic controls, and the electromechanical sample changer assembly.

Referring initially to the perspective view of the system illustrated in FIG. 1, the major components of the system are shown, including the sample changer assembly 10, the instrument rack 12 containing the basic electronics and the data printer 14, illustrated in the form of a teletypewriter. The sample changer assembly 10, the operation of which will be described in greater detail in connection with FIG. 2, includes the basic electromechanical components designed to select appropriate samples from the sample tubes, perform the mechanical and initial electrical steps relating to cell counting, deliver the cells to the testing stations and conditioning the cell samples thereafter for ultimate radiation detection. These goals are achieved by means of sample changer tray 16 which includes an upper plate 16A designed to accommodate the sample tubes 22 and a lower plate 16B designed to accept the sample filter assemblies 24. The sampling process is performed by means of sampler assembly 18 which, as will be discussed hereinafter, includes a pivotable arm adapted to lower an orifice tube into successive ones of the sample tubes as the sample tray 16 rotates from position to position. In between samplings, sampler assembly 18 elevates the orifice tube out of the sample tube and returns to a rest position during which the orifice tube is cleaned by means of a rinse bath and ultrasonic treatment.

Sample changer assembly 10 also includes radiation detector 20, which is illustrated in FIG. 1 in the form of a cylinder mounted on the rear face of the housing and adapted to be positioned over the filter assemblies 24 as they are rotated to the detection station by sample changer tray 16. Specifically, after sample assembly 18 and its orifice tube to be discussed hereinafter remove a pre-determined number of cells from the appropriate sample tube 22 which has been inserted in an aperture in upper sample plate 16A, internal pumping within assembly 10 delivers these cells, still in their suspension, to a depositor arm projecting out from the housing and elevated above a corresponding sample filter assembly 24. Following draining and drying of the sample in the filter assembly at a second station, it is then transported to the third operational station of assembly 10, namely the radiation detection position immediately beneath the lower surface of detector 20. It is at this point that a radioactive count is made, furnishing the computer with information to yield an appropriate output result based on radioactive level as a function of a pre-determined number of cells.

In FIG. 1, only the significant component elements mounted in instrument rack 12 have been shown. Thus, in addition to various control switches located at the top of the rack, panel 12A is the cell counter, electronically coupled to the sampler assembly 18 and designed to count the number of cells sucked upward from the orifice tube and ultimately deposited on the sample filter assembly 24. This cell counter is generally activated as part of the automatic cycle to be described hereinafter, but can also be activated manually. Panel 12B is the radiation counter which is similarly coupled to radiation detector 20. This counter, which may take the form of a nuclear spectrometer, determines the number of counts in the available time period for a particular sample in a filter assembly 24, following delivery from the draining and heating positions immediately preceding the station beneath detector 20. When the system is informed that a sample has arrived at this radiation detection position, the radioactive counter is activated and the count commences—the count continues until a preset accuracy level is reached, based upon the time of the counting cycle and the number of counts found. At the lower portion of instrument rack 12, block 12C is shown, and this constitutes the central processing unit of the computer which controls the various functions to be described hereinafter. Finally, the data printer 14 may take a variety of forms, but the teletypewriter illustrated is one possible embodiment.

Before the samples are placed on the sample changer assembly 10, it has already been noted that the cells are initially taken from a patient, for example by scraping the cervix of a female patient to obtain a "sampling" of cells. In addition to making a standard Pap smear slide for possible further examination or as a control, the balance of the cells are deposited in a tube of glutaraldehyde, for example a one percent solution in a phosphate buffer. This achieves fixation of the cell sample and insures cell integrity during the balance of the preparation and processing steps. Following fixation, the cell sample is centrifuged and the supernatant decanted. It is then washed in a conventional buffer solution and a suspension of the "cell button" is then formulated by placing the sample in a conventional suspension carrier liquid. Since it is significant to avoid clumping of cells, which interferes with obtaining an accurate cell count, it is advantageous to perform a cell dispersion step to avoid such clumping. The invention achieves such dispersion by ultrasonication, that is exposure of the fixed and suspended cells to high frequency sound waves, for example at the frequency of 55 kilocycles. This ultrasonication gives a satisfactory suspension of single cells and permits the ultimate counting called for herein.

In order to "tag" the cells with an appropriate radioactive element, the stain or biochemical used is initially rendered radioactive. The stain disclosed herein should preferably be a nucleic stain, i.e., one which is attracted to the nuclei of cells, but since the visual approach is not being relied on primarily, it is the radioactive parameter associated with the stain which is significant in evaluating the radioactive level. The stain used in this invention is acridine orange which has been made radioactive by substitution of a $C^{14}$ atom in the five position of the molecule. The radioactive acridine orange stain is deposited in the sample tube with the cell suspension and following a staining period, the excess unbound stain is removed by placing the tube in a centrifuge and decanting the supernatant liquid. A final step prior to presentation of a sample to the system is to wash the suspension, for example with distilled water. Each of the treated samples is thereby in an electrolytic suspension, with the integrity of the cells intact and the cells also unclumped and available to be presented on an individual cell-by-cell basis to the counting apparatus.

Figure 2:
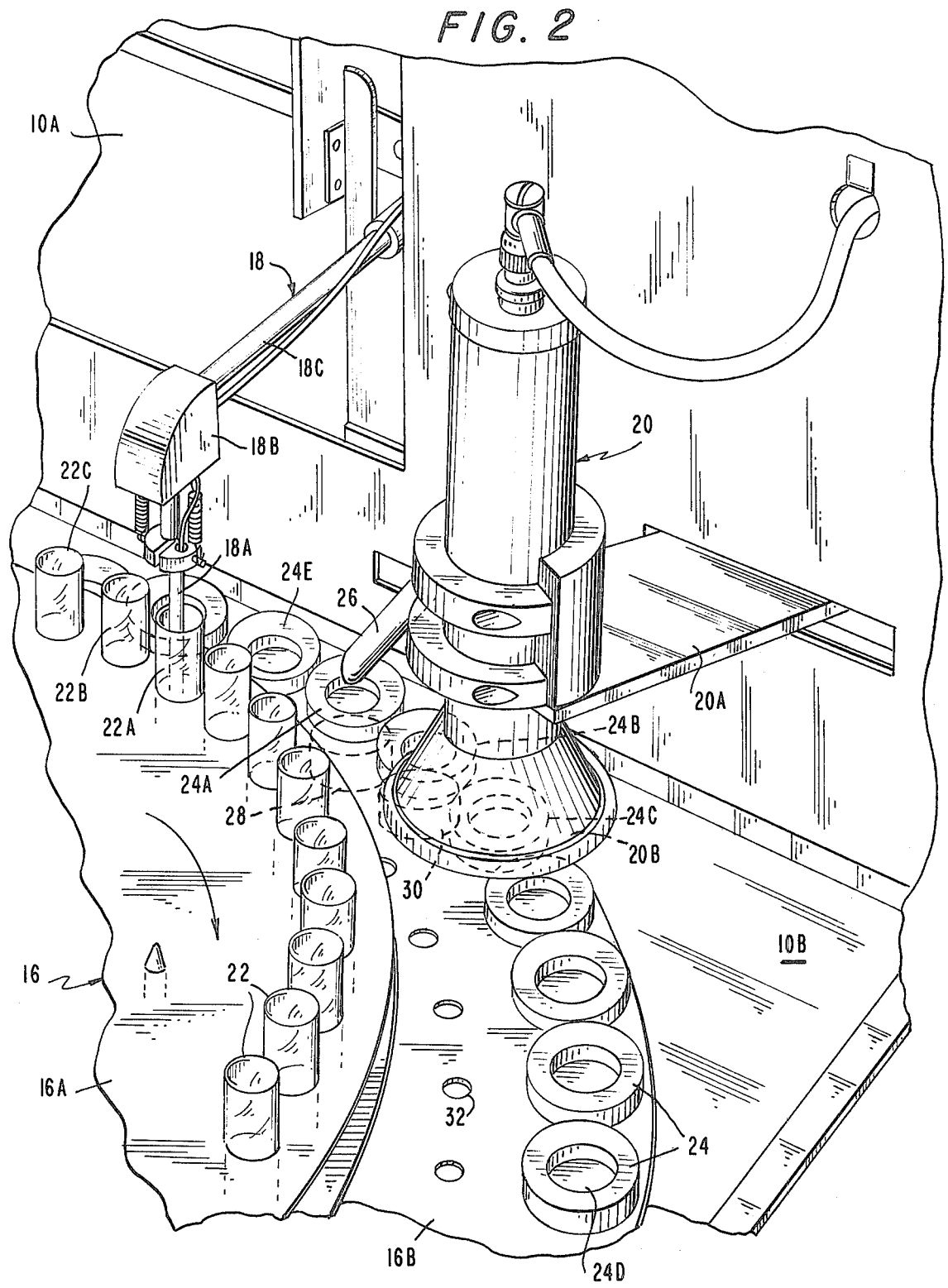
FIG. 2 is an enlarged fragmentary view of a portion of the sample changer assembly, showing the sample tray and its test tubes and filter assemblies, as well as the sample depositor and radiation detector.

The sample tubes 22 containing the cells in suspension as described above are placed into suitable apertures therefor in upper plate 16A of sample changer tray 16. Considering FIG. 2 along with FIG. 1, it is noted that the lower plate 16B includes receptacles to receive and hold sample filter assemblies 24. Each sample filter assembly 24 corresponds to its adjacent sample tube 22 in the same relative position on the upper sample plate 16A. Within each sample filter assembly 24 is a suitable paper filter for receiving thereon the cells withdrawn from sample tubes 22. Such filter paper is available conventionally and may be of the Millipore or of the Nuclepore type. Sampler assembly 18 is shown in FIG. 2 as having its vertical orifice tube 18A in a first sample tube 22A. Under the influence of a peristaltic pump (not shown in FIG. 2), the suspension within sample tubes 22 is sucked up through orifice tube 18A and delivered via horizontal arm 18C to a depositing arm 26. In the course of passing the small orifice at the lower tip of tube 18A, a pulse is generated for each cell of a pre-determined size which passes the orifice, thereby reducing spurious "debris" counts; this is achieved by having one electrode of sampler assembly 18 adjacent to the orifice and the other electrode at the top of the orifice tube, enclosed within sampler arm cover 18B. Each pulse is received by cell counter 12A in instrument rack 12 and is noted on appropriate counter panels and held within the memory of central processing unit 12C. The end step of the cell counting process is the deposition of the pre-determined number of cells by depositing arm 26 onto filter paper 24D of the filter assembly 24 which is located beneath arm 26 at the time. As illustrated in FIG. 2, filter assembly 24A is shown in the first operational position or station of sample changer assembly 10.

Immediately beneath the lower plate 16B of tray 16 is a filtering vacuum pump 28, shown in broken lines in FIG. 2. After the pre-determined number of cells have been deposited on the filter assembly from depositing arm 26, vacuum pump 28 is activated to draw down the liquid remaining on filter paper 24D within the filter assembly 24. The pump 28 is designed to mate with the underside of each filter assembly 24 as it moves into position in operational position 1, and there are appropriate perforations in the underside of filter assembly 24 to permit the drawing of vacuum down through the filter paper 24D. The vacuum pump achieves a substantial draining of the cell sample in this first position.

The sampler assembly 18 has, by this time, been withdrawn from the first sample tube and has pivoted back to a "rest" position within housing 10A. At this rest position, the orifice tube 18A is deposited in an appropriate saline rinse solution and is exposed to a brief ultrasonication cycle to clean the orifice and its small tip. It remains at this location until the sample changer rotates the first sample filter assembly 24 to the second station. At this second station, the underside of the first sample filter assembly 24 is presented with a heater and dryer apparatus which is also beneath the lower plate 16B of sample tray 16. This heater, indicated at 30 in broken lines in FIG. 2, completes the drying cycle with respect to the sample which has previously been deposited on filter paper 24D of sample filter assembly 24. At the same time, sampler assembly 18 can be withdrawing its next sample from the following sample tube 22 which has rotated into position beneath orifice tube 18A as sample tray 16 has rotated. When the drying cycle has been completed, a further rotation of sample tray 16 occurs, bringing the first sample filter assembly 24 to a third operational station which is beneath the active surface 20B of radiation detector 20. This detector, which may take the form of a crystal and photomultiplier tube, can be pivoted into position by means of carrying arm 20A which is mounted within the rear upright housing of sample changer assembly 10. The radiation count is made with respect to the sample within assembly 24 and this data is furnished to radiation counter 12B in instrument rack 12.

The data concerning the number of cells deposited on a particular filter assembly 24, as well as concerning the radiation count with respect to that sample, are fed to the central processing unit 12C at the instrument rack 12. This computer also controls the minimum number of cells to be taken by sampler 18 and the necessary radiation count to achieve the pre-set accuracy for which this system has been programmed. For example, since it is anticipated that there will be relatively low activity levels of the $C^{14}$ absorbed on the cells, the minimum number of cells to be taken by means of orifice 18A of sampler assembly 18 will be about 50,000–150,000 cells, with the radiation count lasting about 2 minutes. Other parameters to be controlled by central processing unit 12C are the maximum time permitted for pumping of the withdrawn sample, the acceptable accuracy rate and the limit of the ultimate result to evaluate positive activity of the sample. This data is processed in central processing unit 12C and the results printed out on the printout sheet of data printer 14.

Figure 3:
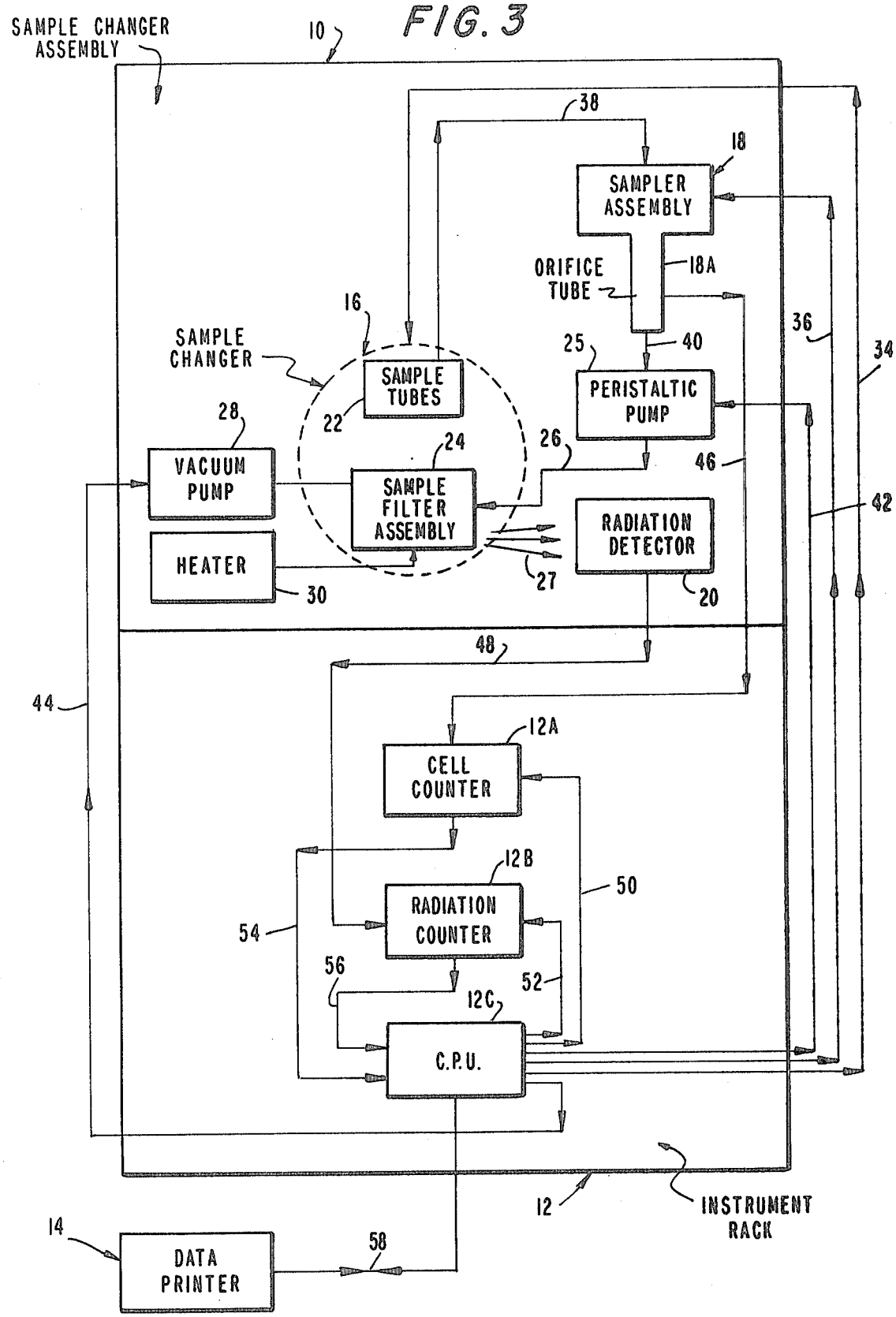
FIG. 3 is a block diagram of the overall system of the invention, showing the interrelationship of the electronic and mechanical components of the system of the invention.

The following is a description of a typical automatic cycle of operation of the system of the invention, referring to the overall view of the invention illustrated in FIG. 1, the specific fragmentary view of the sample changer assembly shown in FIG. 2 and the block diagram shown in FIG. 3. Following the placement of a load of sample tubes 22 in their receptacles in upper plate 16A of sample tray 16, the system is initiated by selecting the automatic mode, the first step of which is to activate sampler assembly 18. Regardless of the previous position of the assembly (i.e., with orifice tube 18A in a sample tube 22 or at some intermediate position), sampler assembly 18 will be caused to return to its rinse bath at the rest position within rear housing 10A. This will be achieved by the withdrawal of orifice tube 18A if it had been within a sample tube 22 and the pivoting of sampler arm 18C back towards housing 10A. Orifice tube 18A will then be deposited in the rinse solution (not shown) which preferably contains filtered saline solution. Upon such deposition, saline from the rinse bath will be pumped through the orifice tube for a brief period of time to cleanse the tube and to prepare it for the first sample.

Althrough there is a basic sequence of steps by which the system will ordinarily operate, additional instructions may be supplied at the commencement of the cycle from data printer 14. Thus, if there are any changes to be made in usual system parameters such as maximum pumping time, maximum total time, acceptable accuracy, the limit for positive activity or an insertion of names associated with the samples, this can be accomplished at the beginning of the cycle. After this "conversation", if any, has taken place, the first automatic determination made by the system is that a tray 16 of samples 22 is in fact in position on the top of horizontal housing 10B of sample changer assembly 10. Since the tray can be removed for loading the samples, the positive response will only be received after the sample tubes have been placed into their receptacles on sample plate 16A and the tray returned to its position atop housing 10B. When it has been ascertained that there is indeed a sample tray 16 in place, a motor (not shown) controlled from within housing 10B will commence preliminary rotation of sample tray 16 in order to index it to the first sample position on the tray. After the system has also determined that its other components, including radiation detector 20 and depositor arm 26 are "ready", sampler assembly 18 is activated to commence withdrawing cells from the first sample tube 22A (FIG. 2). Arm 18C pivots to the position illustrated in FIG. 2, perpendicular to housing 10A, and orifice tube 18A is then lowered into the sample tube. Upon lowering of orifice tube 18A, a peristaltic pump shown as block 25 in FIG. 3 is activated to draw suction from orifice 18A and to thereby pump the cells through the orifice tube and into the system. A peristaltic pump, of the type manufactured by Cole-Parmer Instrument & Equipment Co. of Chicago, Ill., is utilized in order to avoid contamination of the sample; as is known, such a pump operates by applying peristaltic-type pressure external to a fluid transmitting tube and thereby advances the liquid to a specific location without coming in contact with the liquid itself. As each cell passes the tip of the orifice, a pulse is generated and is counted as an additional cell in cell counter 12A of instrument rack 12. The peristaltic pump 25 then transports the cells to depositing arm 26, which projects out from housing 10A and deposits the cell samples in the sample filter assembly 24A which is in the first operational position, as illustrated in FIG. 2. The pumping action under the influence of pump 25 will continue until either the predetermined number of cells is reached (for example, 100,000 cells) or the maximum pumping time per sample has elapsed, depending upon which occurs first. At that point, the central processing unit 12C instructs pump 25 to terminate its pumping action and sampler assembly 18 is then returned to its rest position. This is achieved by elevating orifice tube 18A out of the first sample tube 22A, pivoting arm 18C back to housing 10A and lowering orifice tube 18A into the rinse bath. As sampler assembly 18 is achieving this return movement, a brief suction action under the influence of pump 25 occurs, thereby drawing a small air bubble into the system, which is detected by orifice tube 18A and constitutes a "mark" between samples. In order to prepare sampler assembly 18 for the next cycle, the saline rinsing solution is then drawn into orifice tube 18A and pumping action proceeds for a brief period, followed by ultrasonication of the orifice tube 18A to provide a cleansing action.

Accordingly, the first sample filter assembly 24A now has on its contained filter paper 24D the pre-determined number of cells from the sample tube 22 and as well as suspension liquid and some saline rinse solution. While the filter paper does permit some of the now undesired liquid to drain therethrough and to be removed from the system, not all of the liquid is removed. Accordingly, vacuum pump 28 is provided beneath the first operational position of sample filter assembly 24A to draw vacuum down and to achieve substantial draining of the sample for a pre-determined time interval. When the vacuum pump draining cycle has been completed, central processing unit 12C instructs sample tray 16 to be advanced to the next position. This will bring a second sample tube 22B into the location adapted to be sampled by sampler assembly 18 and will bring the first sample filter assembly 24A to the second operational position clockwise of the position illustrated in FIG. 2. At that position, with the sample filter assembly now being identified as 24B in FIG. 2, the filter assembly is in position above a heating and drying unit 30 beneath the sample plate 16B. The heater 30 completes the drying cycle to reduce self-absorption of the specimen on filter paper 24D and permits more accurate radioactive counts to be recorded at the next position. At the same time, sampler assembly 18 has pivoted into position over the next sample tube 22B. Orifice tube 18A is then lowered into that sample tube and the pumping, counting and deposition described above with respect to the first sample now occur with respect to the second sample. These cells are deposited in the next succesive sample filter assembly 24E as shown in FIG. 2, which by this time has rotated into position under depositor arm 26.

Following a pre-determined heat cycle applied from heater 30, and the completion of the taking of the second sample from sample tube 22B by sampler assembly 18, sample tray 16 is again rotated, bringing the first sample filter assembly 24A to a third operational position, designated as 24C in FIG. 2. At the same time, the second sample filter assembly 24E now moves to the second operational station where the action of heater 30 dries that sample; similarly, a third sample tube 22C is now in position under sampler assembly 18 which can now be instructed to return to its active position from the rinse solution at the rest location within housing 10A. Upon arrival at the third operational station, the sample in filter assembly 24C is presented to the underlying face 20B of radiation detector 20. The radiation count then commences, with each count being fed to counter 12C at instrument rack 12, and also being stored in memory. Depending upon the activity level of the specimen being tested by detector 20, the count will continue in order to achieve the pre-set accuracy called for by the system. As has already been noted, with a sample of approximately 50,000–150,000 cells, the preset accuracy will generally be obtained, and this will require approximately 2 minutes. If a sample is particularly low in radioactive level, the count may continue for an additional time period, subject to the maximum time limitation imposed by the program of central processing unit 12C. When the radiation count has been completed by satisfaction of the various system parameters, a data compilation is obtained by data printer 14, based on information supplied to it from instrument rack 12 under the control of central processing unit 12C. A typical printout of the system can include the number of the sample, the radioactive count normalized on a per cell per unit time basis, the accuracy level obtained, the total number of cells and the total radioactive count. If, despite achieving the maximum pumping time, an insufficient number of cells was extracted from the specimen, printout comment will be given to the effect that the specimen was too dilute. Similarly, if the predetermined accuracy level was not reached in the maximum total time period allotted for the specimen, results will be given by the data printer 14, with an appropriate comment indicating that the specimen was of such low activity that the accuracy is questionable.

The significant result which is sought by the system is whether or not a particular specimen is "positive", "negative" or "suspicious". This evaluation is based on the radioactive count normalized by the number of cells per unit time in the sample. If this figure exceeds a pre-determined quantity, which has been set on the basis of experimental testing and careful evaluation, the data printer 14 will indicate "positive" with respect to a given specimen. On the other hand, if the radioactive count does not exceed that number, the specimen will be considered "negative". The system can of course also be programmed to indicate "suspicious" for any specimen which falls into a certain tolerance range near the pre-set "positive" quantity.

Following the radioactive count and printout with respect to the sample which had been advanced to the third operational position at filter assembly 24C in FIG. 2, the sample changer again rotates and brings a further sample tube 22 into position under orifice tube 18A, and advances the preceding sample filter assembly 24 to the heating and drying position at 24B and the next preceding sample filter assembly to the radioactive count position at 24C. The sampler assembly 18 then lower its orifice tube into the next sample tube and the cycle continues until all of the samples have been tested. The arrival of the sample tray 16 at the final sample can be indicated by the placement of an appropriate pin in a receptacle 32 provided for that purpose in lower plate 16B of sample tray 16. Switch means (not shown) beneath plate 16B will be contacted by the pin when sample tray 16 presents the final sample tube 22 for sampling. Following the sampling of this last sample, the functional steps at the three operational stations of the system will continue only until the last sample has advanced to the sample filter assembly position at 24C, and once the radiation count with respect to that sample has been taken by detector 20, the cycle will have been completed. There are other occurrences which will also cause the system to pause or stop, awaiting further instructions, such as the blockage of the orifice at the tip of tube 18A or if the rinse bath in which orifice tube 18A is placed between samplings becomes contaminated. The data printer 14 will thereupon be activated to provide a readout message seeking additional instructions or corrective action.

The block diagram of FIG. 3 illustrates the functional relationships of the various component parts of the system, with the major blocks as shown in FIG. 1 being illustrated, namely the sample changer assembly 10, the instrument rack 12 and the data printer 14. Within sample changer 10 is the sample changer tray 16, which principally comprises sample tubes 22 and sample filter assemblies 24. The rotation of sample changer tray 16 is under the control of central processing unit 12C, as indicated by the connecting arrow line 34. When the orifice tube 18A of sampler assembly 18 is lowered into sample tubes 22, sampling commences and cells are drawn along representative line 38 into the sampler assembly under the influence of peristaltic pump 25; this pumping action is indicated by means of line 40.

Depositor arm 26, which is shown in FIG. 2, is illustrated in representative form by the line connecting peristaltic pump 25 and sample filter assembly 24 in FIG. 3. The pumping action of pump 25 draws the samples up from orifice tube 18A and delivers the cells, together with the liquid suspension, to the appropriate sample filter assembly 24. The action of peristaltic pump 25 is started and stopped under the influence of central processing unit 12C, as indicated by control line 42. When the sample changer is in its first operational position, and the cells of the first sample have been deposited on the first sample filter assembly 24, vacuum pump 28 is activated under the influence of central processing unit 12C, as indicated by control lead 44. The vacuum pump 28, located beneath the first sample filter assembly position, drains the sample of much of its liquid and following a pre-determined vacuum drawing cycle, sample changer 16 rotates to a second position, whereby the drained sample filter assembly is then placed over localized heater 30. When the heating and drying cycle has been completed, rotation of the sample changer tray 16 continues, to present the sample filter assembly to radiation detector 20.

Information is supplied to the principal component blocks of instrument rack 12 from orifice tube 18A, which supplies the cell count information to cell counter 12A along lead 46. Similarly, the radiation 27 emanating from the drained and dried sample filter assemblies is indicated at the lower portion of sample changer 16 in FIG. 3 as being detected by radiation detector 20. This radioactive information is supplied to radiation counter 12B in instrument rack 12 over symbolic lead 48. Both cell counter 12A and radiation counter 12B are, of course, also controlled by central processing unit 12C, as indicated by symbolic control leads 50 and 52 respectively, while the output information from cell counter 12A and radiation counter 12B are stored in central processing unit 12C over symbolic leads 54 and 56 respectively.

Data printer 14 communicates with central processing unit 12C over bi-directional communication channel 58 connecting blocks 12 and 14 in FIG. 3. This permits the data taken from a group of samples to be provided to the data printer 14 for readout by supervisory personnel, and also for additional instructions or corrective action to be read into the system under the control of data printer 14, which supplies this information to central processing unit 12C.

The foregoing system has been shown to be capable of automating a number of important steps in the performing of radioactive counts on cells. On the basis of relatively straightformward instructions supplied periodically by operators through data printer 14, the system can be utilized to customize the invention for local testing standards, which may vary somewhat depending upon the groups being tested, the nature of the cells and the like. Since patients' names can also be inserted along with sample numbers, an extra precaution is also provided against mistakes in patient identification, leading to serious diagnostic errors. The system can also be arranged to operate manually, with the computer off line. While the system may not frequently be used in the manual mode, it may be desirable to do so on occasion for testing purposes and for servicing and cleaning the system or replacing certain components thereof.

It is to be understood that the foregoing embodiments are merely illustrative of the application of the principles of this invention. Numerous variations may be devised by those skilled in the art without departing from the spirit or scope of the invention.

What is claimed is:

1. A method for analyzing cells for determination of cell character, comprising the steps of selecting a sample of cells, placing the cells in a fixative solution to form a suspension, ultrasonicating the cells under conditions to achieve dispersion of cells without disrupting cell membrane integrity, incorporating in the suspension a radioactive biochemical which attaches to at least a portion of the cells, counting a pre-determined number of cells withdrawn from the radioactive suspension, depositing said counted cells at a draining location, transporting said counted and drained cells to a drying location and to a radioactive detection location, performing a radioactive count on said cells at said radioactive detection location and comparing said radioactive count in normalized form with a pre-determined setting to evaluate said sample to determine the character of said cells.

2. The method defined by claim 1 wherein said cell counting, depositing, transporting, draining, drying, radioactive detecting and comparing steps are performed under computer control, and said radioactive biochemical is acridine orange.

3. The method defined by claim 1 wherein said counting step includes analyzing said cells for size and including in the cell count only cells within a pre-determined size range.

* * * * *